United States Patent [19]

Morris et al.

[11] Patent Number: 4,938,593

[45] Date of Patent: Jul. 3, 1990

[54] PHOTOTHERMAL DENSITOMETER FOR READING ELECTROPHORESIS GELS

[75] Inventors: Michael D. Morris; Konan Peck, both of Ann Arbor, Mich.

[73] Assignee: The Regents of the University of Michigan, Ann Arbor, Mich.

[21] Appl. No.: 226,627

[22] Filed: Aug. 10, 1988

Related U.S. Application Data

[63] Continuation-in-part of Ser. No. 8,739, Jan. 30, 1987, abandoned.

[51] Int. Cl.⁵ .................... G01J 3/42; G01N 21/41
[52] U.S. Cl. ......................... 356/344; 356/432
[58] Field of Search ............... 356/432, 432 T, 344

[56] References Cited

U.S. PATENT DOCUMENTS

| | | | |
|---|---|---|---|
| 4,243,327 | 1/1981 | Frosch et al. | 356/432 |
| 4,299,494 | 11/1981 | Badoz et al. | 356/432 |
| 4,540,285 | 9/1985 | Amer | 356/432 |
| 4,591,272 | 5/1986 | Morris et al. | 356/344 |

OTHER PUBLICATIONS

Kohanzadek et al., "Measurement of Refractive Index Change with Temperature Using Thermal Self-Phase Modulation", *Applied Optics*, vol. 12, No. 7 (Jul. 1973), pp. 1584–1587.

Jackson et al., "Photothermal Deflection Spectroscopy and Detection", *Applied Optics*, vol. 20, No. 8 (15 Apr. 1981), pp. 1333–1344.

Harris, Jr., "Photothermal Methods for Detection of Molecules in Liquids", *Optic News*, (Oct. 1986), pp. 8–15.

*Primary Examiner*—Richard A. Rosenberger
*Attorney, Agent, or Firm*—Harness, Dickey & Pierce

[57] ABSTRACT

A densitometer apparatus for evaluating electrophoresis gel samples based on photothermal techniques. In accordance with this invention, electrophoresis gels are characterized by passing a heating light beam through the gel at a particular location. Light absorbed by the presence of staining dyes in that area causes heat evolution which generates a local index of refraction variation or a "thermal lens". A probe beam is passed through the sample in the area of the thermal lens a predetermined period of time after it is generated and the modification to the beam caused by the thermal lens is evaluated. For example, defocusing of the probe beam can be sensed by a detector which receives transmitted light through a limiting aperture. Various means of separating the heating and probe beams are disclosed, including use of separate lasers, crossed beams, modulation by plane of polarization, etc. One embodiment of this invention is particularly adapted for characterizing dry gels in which the heating beam is absorbed by the sample and the probe beam passes across the sample and is modified by a thermal lens generated in the air above the sample. Several embodiments are related to means for offsetting the probe beam from the heating beam for use with samples that are swept by the photothermal techniques in accordance with this invention offer advantages in terms of sensitivity over conventional transmission-type densitometers. These advantages enable increased sensitivity and facilitate the use of simplified staining techniques.

20 Claims, 4 Drawing Sheets

_Fig-3_

_Fig-4_

_Fig-7_

_Fig-8_

PHOTOTHERMAL DENSITOMETER FOR READING ELECTROPHORESIS GELS

CROSS-REFERENCE TO RELATED APPLICATIONS

This application is a continuation-in-part of copending application Ser. No. 8,739, filed on Jan. 30, 1987, now abandoned having a title and assignee common to this application.

BACKGROUND OF THE INVENTION

This invention relates to densitometers particularly adapted for detection and quantification of molecules separated by gel electrophoresis using photothermal techniques.

Electrophoresis is an analytical technique widely used by medical researchers, biochemists and molecular biologists for characterization of large atomic weight charged molecules, such as proteins and nucleic acids.

In one type of electrophoresis procedure, a sample to be characterized is deposited at an area of a slab of gel material, made for example, from a polyacrylamide which provides a matrix through which the sample molecules can migrate. The gel is exposed to a DC electrical field which causes charged molecules of the sample to migrate through the gel. The gel material inherently traps smaller molecules less efficiently than larger molecules. Accordingly, after a period of exposure to the electrical field, molecules are deposited at certain regions of the gel in accordance with their moledular weight, size, structure and charge.

Most of the molecules of interest for characterization by electrophoresis procedures are transparent in the visible and near ultraviolet range. Their ultraviolet absorption is masked by the absorption of constituents of the gel medium. Therefore, once the molecules have migrated within the electrophoresis gel, they are stained to permit their detection by optical techniques. Presently, transmission-type densitometers are used to characterize the stained areas of the gel. In these devices, light from a low power laser, or tungsten or deuterium lamp is passed through the sample and the absorption of the light caused by the stained spot on the gel is evaluated. Absorption is determined simply by the difference between detected light with and without the sample interrupting the light beam. Direct transmission-type densitometers have inherent limitations in their detection limits which are a function of optical noise and detector sensitivity.

Due to the sensitivity limits of conventional transmission-type densitometers, the staining procedure must produce an optically dense patch on the gel sample. In one present staining procedure, the gel is soaked with silver nitrate and the ionic silver is reduced to metallic silver which is deposited in the areas where the organic molecules are present. For many classes of organic molecules, silver staining techniques result in optically dense patches appearing on the electrophoresis gel which can be quantified using conventional light transmission techniques. Although silver staining of electrophoresis gels provides meaningful data, the procedure suffers from several disadvantages. Silver staining procedures are tedius, time consuming and complex. The reagents employed for silver staining are furthermore relatively expensive. Moreover, silver stains cannot be used to stain all types of molecules.

Another technique for imaging patches of organic molecules on electrophoresis gels is autoradiography. This procedure produces high optical density on photographic film contacting the gel regions in the areas of various classes or organic molecules. Autoradiography procedures are even more complex and tedious than silver staining. The procedure is however, presently required for characterizing molecules which cannot be stained using other procedures to a level within the detection limits of conventional transmisson densitometers.

Still another staining technique for electrophoresis gels uses Coomassie Brilliant Blue dyes. These dyes are inexpensive and simple to apply. Unfortunately, the optical density produced by Coomassie Brilliant Blue dyes for some samples is not sufficient to generate adequate absorption for existing transmission types densitometer devices, and accordingly, the use of such dyes has been limited in the past where high sensitivity is required.

Accordingly, there is a need to provide a densitometer apparatus for reading electrophoresis gels which provides higher sensitivity, thus facilitating simplified gel staining procedures.

SUMMARY OF THE INVENTION

In accordance with the present invention, photothermal measurement techniques are employed which provide an indirect measure of absorption within a stained electrophoresis gel sample. In these techniques, a laser heating beam passes through the gel sample which becomes locally heated in accordance with light absorption within the gel, which is a function of the density of stain in that area. This heat evolution causes local refractive index variations, thereby generating a thermally induced optical lens (i.e., a "thermal lens"). A probe beam is passed through the sample in the area of the thermal lens and the modificaton of the probe beam caused by the presence of the lens is quantified as an indirect measure of light absorption. For example, by passing the probe beam emitted from the sample past a limiting aperture, the defocusing of the beam caused by refraction through the thermal lens can be evaluated, which is a function of light absorption within the sample. Such photothermal techniques have been shown to provide considerable improvements (one order of magnitude or more) in sensitivity as compared with direct absorption measurements.

The electrophoresis gel densitometer devices in accordance with several embodiments of the present invention employ a modulated laser heating beam which heats the sample to generate the thermal lens, and a separate lower power laser probe beam which passes through the sample in the area of the generated thermal lens. The probe beams emitted from the sample is evaluated by a detector and associated signal processing devices.

Due to the enhanced sensitivity of the photothermal techniques disclosed herein, dyes such as Coomassie Brilliant Blue can be used in situations where silver staining is now employed. Accordingly, such stains can be used with increased frequency; thereby simplifying staining techniques and reducing costs associated with characterizing electrophoresis gels. Similarly, in certain situations, the techniques enable use of silver staining in place of autoradiography.

Several of the embodiments disclosed herein are applicable to wet gels in which a heating beam and probe beam are transmitted through the sample. Dry gels are not readily amenable to thermal lens densitometry. Dry gels are customarily dried by suction by placing them in a chamber on a filter paper support. As the gel dries, its surface acquires an imprint of the fiber structure of the paper. The dry gel surface therefore behaves like a random array of tiny lenses and prisms. Although the thermal lens signals which can be produced by thermal lens densitometry of dry gels are large, the surface irregularities of the sample caused by random deflection and magnification of the laser probe beam makes the signals noisy. In accordance with one embodiment of this invention, dried gels are characterized by passing a probe beam across its surface along an area subjected to a heating laser beam; thus, generating a thermal lens in the air adjacent the sample.

Electrophoresis gels are typically evaluated by scanning them in a systematic fashion. Because many points on the gel must be measured, the densitometer device must be capable of scanning at a rate of 10 to 100 millimeters per second or faster if possible. In densitometer devices in accordance with the present invention, there is a rise time in the heat generated through absorption of the heating beam as it passes through the gel sample. In systems in which the probe and heating beams are coincident and are scanned across the gel surface, the rise time phenomenon causes the induced thermal lens to be displaced behind the region being evaluated by the probe team, with respect to the direction of relative translation. Accordingly, several embodiments of the present invention provide means for displacing the points of intersection of the probe and heating beams through the gel sample. Specifically, the probe beam is displaced behind the heating beam with respect to the direction of relative translation such that the regions being heated are probed after they are subjected to the heating effect of the heating beam.

DETAILED DESCRIPTION OF THE INVENTION

Figure 1:
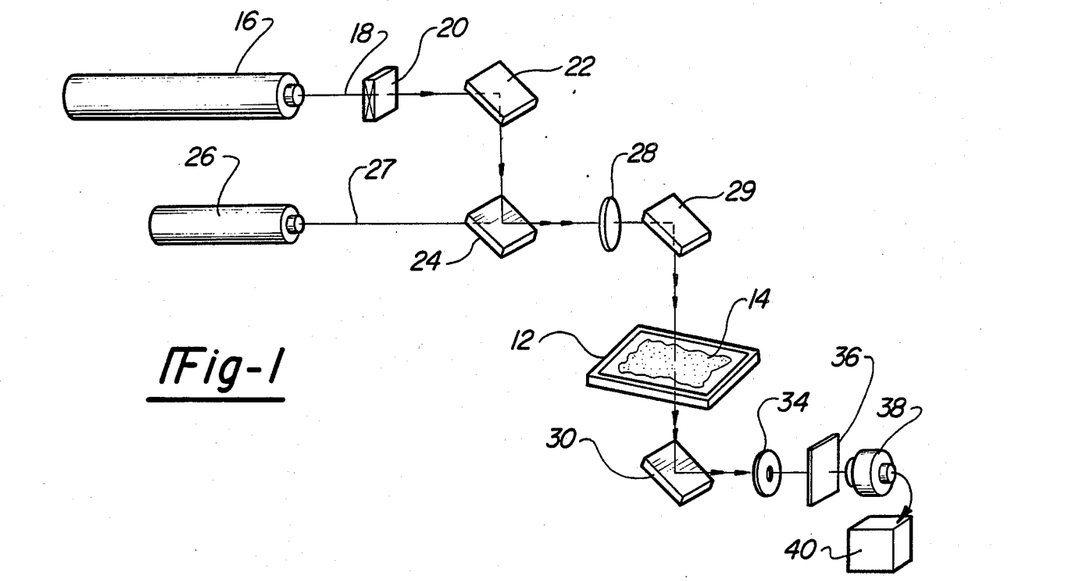
FIG. 1 is a pictorial representation of a densitometer apparatus in accordance with a first embodiment of this invention which employs axial heating and probe beams.

A densitometer apparatus for reading electrophoresis gel samples in accordance with a first embodiment of this invention is represented pictorially in FIG. 1 and is designated generally by reference number 10. Apparatus 10 includes a movable translation stage 12 which can be incrementally indexed to enable characterization of gel 14 at precise locations. Translation stage 12 includes means for mounting gel 14, which is preferably cast in the form of a thin slab. Various gel materials may be employed in electrophoresis procedures, such as polyacrylamides. Gel 14 is subjected to the electrophoresis separation process and may be stained with various agents, such as Coomassie Brilliant Blue dyes, silver stain, etc.

The photothermal technique employed in connection with this embodiment of the invention utilizes a pair of laser sources. Laser 16 provides a heating beam 18 which inputs energy at a precise location within gel 14 to generate a thermal lens. Various types of lasers may be used to generate heating beam 18. It is necessary to select a laser for heating beam 18 having a significant output within the range of absorption by the dye being used, while readily transmitting through unstained gel. For example, the absorbance versus wavelength characteristics of typical Coomassie Brilliant Blue dyes have a generally gaussian distribution, with half-maxima limits bounded by about 520 and 650 nanometers (nm). The 528 nm emission of an argon ion laser and the 633 nm emission of a helium-neon laser lie within these limits and therefore are suited for use with Coomassie Brilliant Blue dyes. When using silver staining procedures, helium-cadmium lasers would appear useful. These inventors have found that lasers with output power in the 20 to 50 milliwatt range may be employed successfully in connection with this invention.

Heating beam 18 emitted from laser 16 passes through mechanical chopper 20. Chopper 20, or an alternate modulation device, preferably interrupts the light output at a rate of about 7 to 19 hertz. Mirror 22 steers the beam from laser 16 to dichroic mirror 24.

A separate laser 26 is provided to generate probe beam 27 which is passed through any thermal lens generated within the sample and is modified by the thermal lens through refraction. The degree of modification of probe beam 27 is characterized to provide an indirect measure of light absorption within the sample. Various types of lasers may be used for laser 26. It is only necessary that the heating caused by laser 16 generates index of refraction changes in the gel sample. Since for this embodiment it is necessary to separate beams 18 and 27 after they pass through the sample, their frequencies should be significantly different.

The output from laser 26 is directed at dichroic mirror 24 such that beams 18 and 27 from both lasers are combined into a coaxial beam. Lens 28 serves to focus the beams within gel sample 14, and mirror 29 steers the beams. Mirror 30 is located below translation stage 12 and directs the combined beams toward aperture 34 and interference filter 36 which blocks light from laser 16

(which is at a different frequency than that from laser 26). A photodiode or other light sensor 38 is used to measure the intensity of the probe beam 27. A lock-in amplifier 40 is synchronized with chopper 20 and enables the AC component of the signal sensed by detector 38 to be evaluated. This AC component results from generation and partial dissipation of thermal lenses in the gel sample caused by pulsing of heating beam 18 (due to the action of chopper 20). The pulsing actions causes the output signal from sensor 38 to have a partially saw-tooth or ramping characteristic (i.e., AC component). This signal is combined with a signal from lock-in amplifier 40 and filtered to produce a DC level proportional to the density of dye in the target area.

Figure 5:
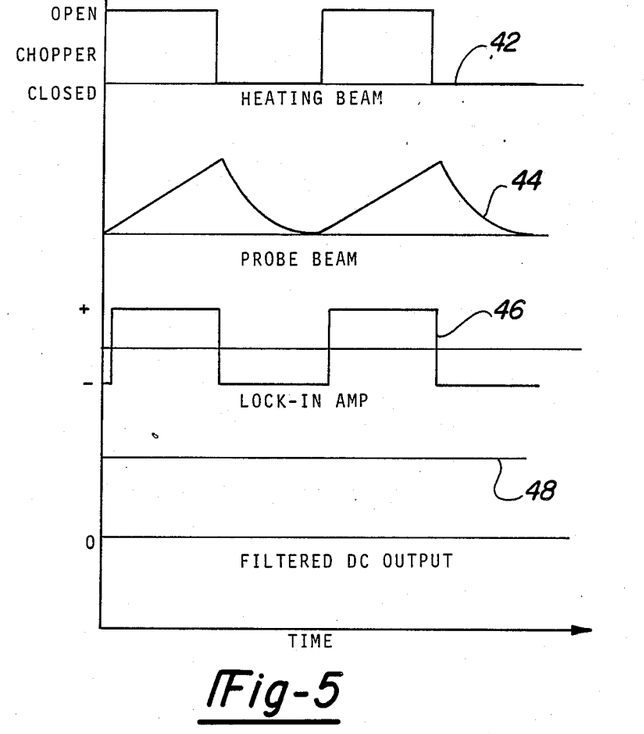
FIG. 5 is a graph showing signal traces of heating and probe beam intensity, lock-in amplifier gating, and output signal for a representative device.

FIG. 5 provides a simplified graphical representation of the intensity of heating beam 18 and probe beam 27, and lock-in amplifier 40 and output signals. Curve 42 shows the square have characteristic of heating beam 18 as it is interrupted by chopper 20. Curve 44 illustrates an example of the probe beam signal detected by sensor 38. The ramping characteristic of curve 44 is caused by the heating of the sample over time when exposed to heating beam 10, and the thermal relaxation which occurs while the heating beam is interrupted. Lock-in amplifier 40 is synchronized with the gating provided by chopper 20 (with a small phase difference to more closely follow curve 44). lock-in amplifier 40 provides the signal of curve 46 which is a square wave bounded by plus one and minus one levels. Curve 46 is multiplied by curve 44, and this signal is filtered to remove AC components. Resulting curve 48 is a DC level which is the system output signal and is related to the density of dye in the target region of gel 14.

In operation, thermal lenses are generated within gel 14 by the energy inputted by laser 16. The modulation frequency of heating laser 16 is chosen to be somewhat above the frequency response range of the generated thermal lens (thereby producing the component mentioned above). The existence of the thermal lenses within gel 14 causes defocusing of the narrow beam from laser 26. The level of defocusing is sensed by detector assembly 32 due to the presence of aperture 34 which is intentionally overflowed to provide a limiting aperture. Translation stage 12 enables gel 14 to be precisely indexed, thus enabling characterization of different areas of the gel. Excellent spatial resolution is provided due to the small focusing of the beams from lasers 16 and 26 (if accompanied with adequate positioning resolution of translation stage 12).

Figure 2:
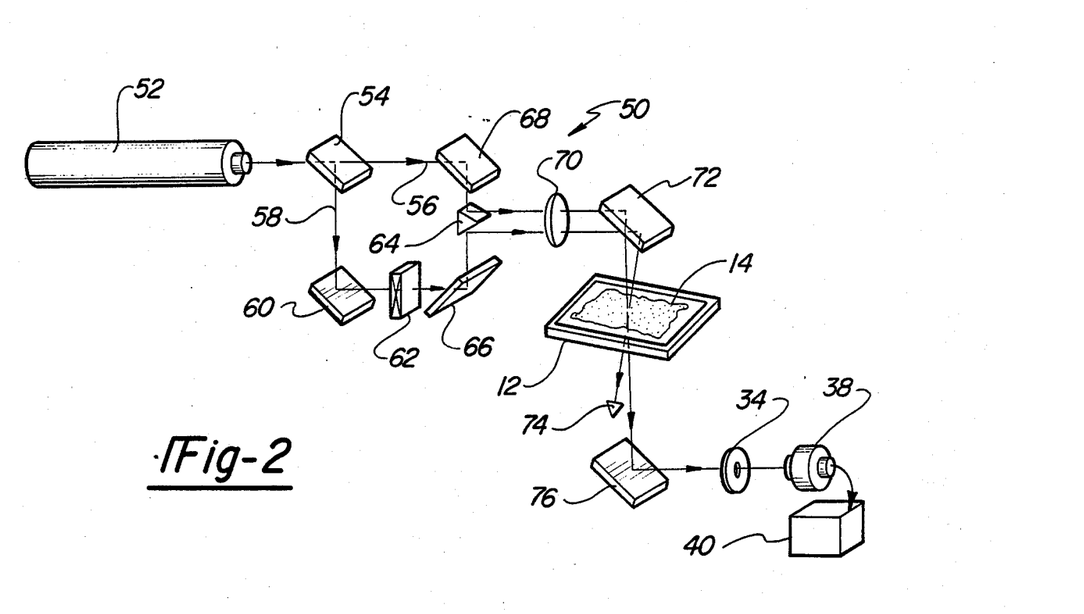
FIG. 2 is a pictorial representation of a densitometer apparatus in accordance with a second embodiment of this invention which utilizes crossing heating and probe beams which are derived from a common laser source.

A densitometer apparatus in accordance with a second embodiment of this invention is illustrated in FIG. 2 and is generally designated by reference number 50. The elements of apparatus 50 (and other embodiments described below) which are identical to elements of apparatus 10 are identified by like reference numbers. In this embodiment, a single laser 52 is employed. Beam splitter 54 separates the light emitted from laser 52 into probe beam 56 and heating beam 58 components. Preferably, the probe beam 56 component is a small fraction of the total output power of laser 52. Heating beam 58 reflects off mirror 60 and passes through mechanical chopper 62. Probe and heating beams 56 and 58 are steered toward right-angle prism 64 by mirrors 66 and 68. The rays are then generally parallel and pass through lens 70 which causes them to intersect as they pass through gel 14. These rays are steered through the sample by mirror 72. A beam stop 74 is provided which absorbs heating beam 58. Mirror 76 steers probe beam 56 toward aperture 34 and detector 38. Furthermore, lock-in amplifier 40 is provided which operates as previously explained. Densitometer 50 is operated in a manner identical to that described in connection with the first embodiment.

Figure 3:
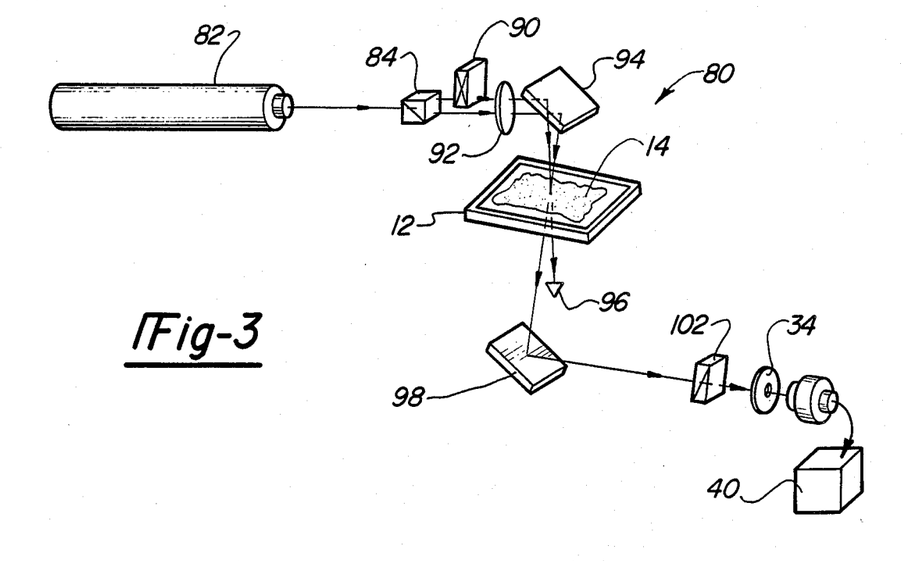
FIG. 3 is a pictorial representation of a densitometer apparatus according to a third embodiment of this invention in which the heating and probe beams are encoded by separation and plane of polarization, and are derived from a common laser source.

FIG. 3 illustrates a densitometer apparatus in accordance with a third embodiment of this invention which is designated by reference number 80. Like the second embodiment, densitometer 80 employs a single laser source 82. In this embodiment, the light emitted by laser 82 is separated by plane of polarization using Wollaston prism 84. Prism 84 provides two physically separated beams having differing orthogonal planes of polarization. The stronger of these polarized components is employed as heating beam 86, and the other output is employed as a probe beam 88. Heating beam 86 passes through chopper 90. Both the beams pass through lens 92 which causes them to intersect within gel 14 as they are steered by mirror 94. Beam stop 96 absorbs heating beam 86. Mirror 98 directs the probe beam 88 to aperture 34 and detector 38. As an additional means of rejecting heating beam 86, Glan prism 102 is employed which filters out light polarized in the direction of that of heating beam 86. Lock-in amplifier 40 is identical in function to that described in connection with the previous embodiments.

Figure 4:
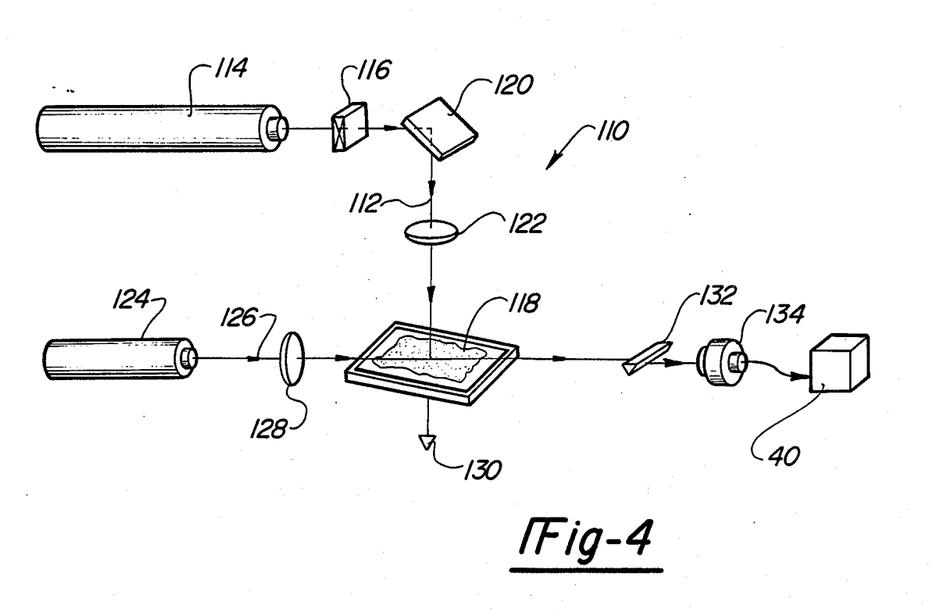
FIG. 4 is a pictorial representation of a densitometer apparatus according to a fourth embodiment of this invention particularly adapted for use with dry gels.

A fourth embodiment of this invention is shown in FIG. 4 which is particularly adapted for characterizing dry gels and is designated by reference number 110. In this embodiment, heating beam 112 emitted from laser 114 passes through chopper 116 and is directed into dry gel sample 118 by mirror 120 and lens 122. Laser 124 emits probe beam 126 which is focused by lens 128 to be oriented so that the beam passes along the surface of dry gel 118. Beam stop 130 is positioned on the opposite side of dry gel sample 118 to absorb heating beam 112. Probe beam 126 is distorted by the thermal lens formed in the air above the dry gel caused by local heating. This thermal lens causes refraction of probe beam 126. Knife edge 132 serves to block probe beam 126 in accordance with its dispersion. The portion of probe beam 126 which is not blocked by knife edge 132 is sensed by detector 134. As with the prior embodiments, the output of detector 134 is transmitted to lock-in amplifier 40. As a variation of this embodiment, knife edge 132 can be eliminated and a linear detector array or position sensing diode substituted for detector 134.

Operation of densitometer apparatus 110 proceeds in a manner similar to the previous embodiments in that translation stage 12 is moved to characterize various portions of dry gel 118. Since probe beam 126 is not transmitted through dry gel 118, surface imperfections in the gel do not adversely affect operation. Although heating beam 112 is affected by these imperfections, that beam is employed only to heat the sample and therefore minor deviations in the beam are inconsequential.

Figure 6:
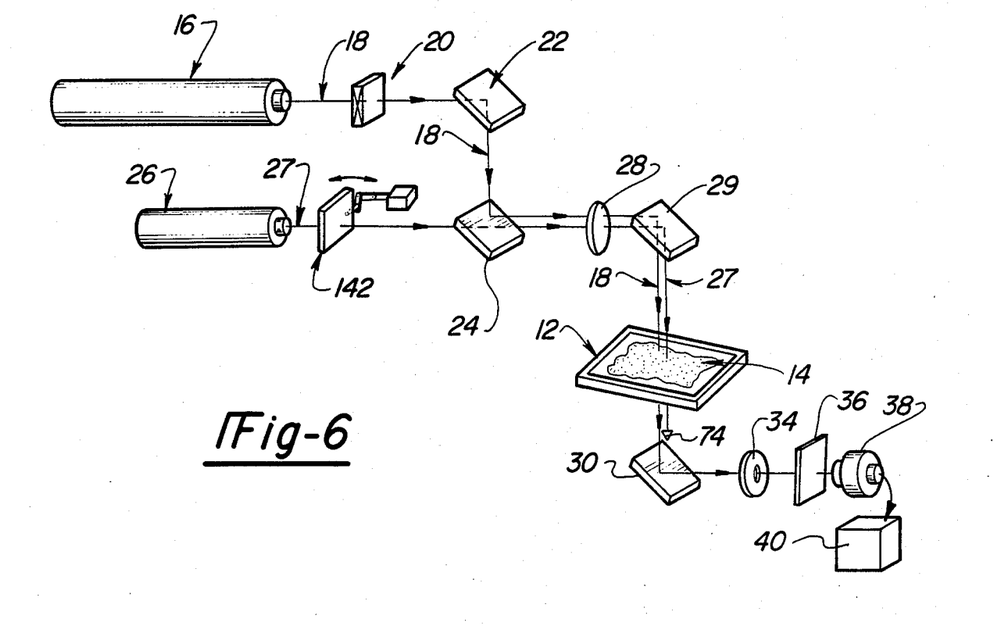
FIG. 6 is a pictorial representation of a densitometer apparatus according to a fifth embodiment of this invention incorporating means for providing bidirectional adjustment of displacement between the probe and heating laser beams incorporating a tilting glass plate.
Figure 7:
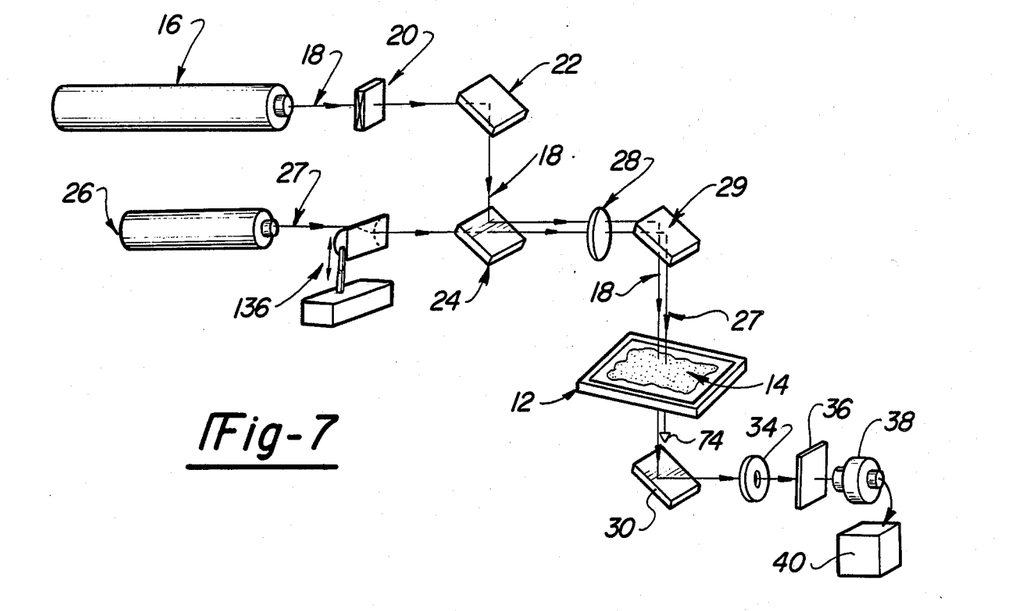
FIG. 7 is a pictorial representation of a densitometer apparatus according to a sixth embodiment of this invention incorporating means for providing bidirectional adjustment of displacement between the probe and heating laser beams incorporating a cylindrical lens.
Figure 8:
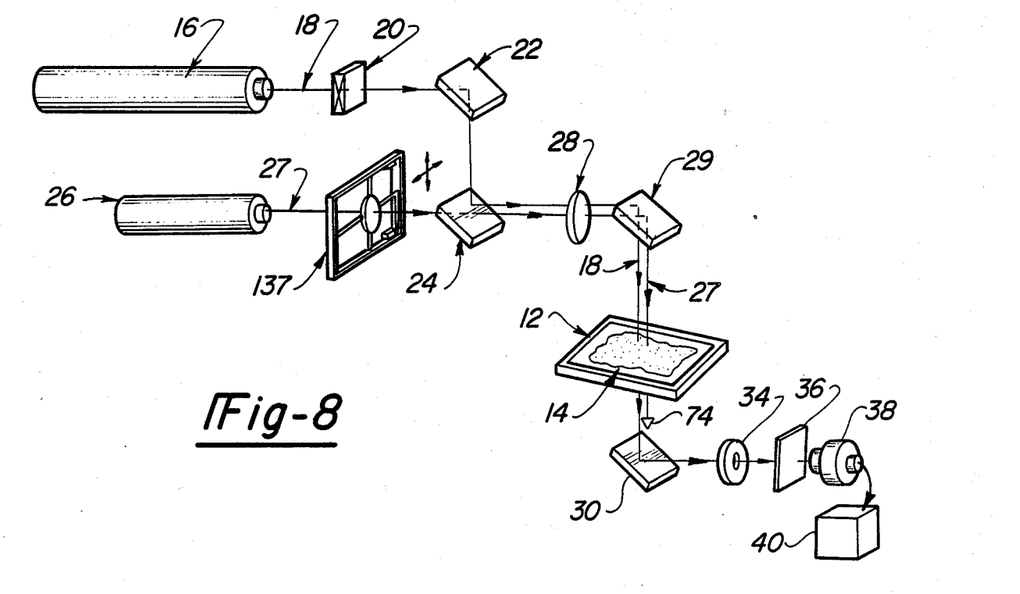
FIG. 8 is a pictorial representation of a densitometer apparatus according to a seventh embodiment of this invention incorporating means for providing adjustment of the displacement between the probe and heating laser beams in any direction within a plane incorporating a biconvex or plano-convex lens.

FIGS. 6 through 8 describe additional embodiments of the present invention which provide for a means of displacing in space the orientation of the probe in heating beams in order to permit the heating beam to lead the probe beam with respect to the direction of translation for use in cases where the gel sample is scanned. The previously described densitometer configurations assume that sample 14 does not move appreciably with respect to the beams during the formation time of the induced thermal lens. As the scan speed approaches and exceeds one millimeter per second, however, that assumption is no longer valid. The rise time of a pulse generated thermal lens in an electrophoresis gel is typically less than one millisecond and the fall time is about ten milliseconds, the exact times depending on the gel composition and the diameter of the focused heating laser beam. If the sample is translated at a rate of one millimeter per second or greater, the optimal measurement region for the probe beam is no longer coincident with the heating laser, but is rather displaced from it at a distance corresponding to a lag time of about one to five milliseconds. At a scan speed of ten millimeters per second, for example, the optimum region for thermal lens evaluation will be located ten to fifteen microns behind the heating laser so that the heating region reaches the probe beam one to five milliseconds after heating. At higher or lower scan speeds, the optimum displacement of heating and probe laser beams will increase or decrease proportionately.

To make a thermal lens densitometer for use with scanned samples, it is necessary to provide a means by which the heating and probe beams can be displaced relative to each other in space, and preferably enable such displacement to be conveniently adjusted. In most cases, it will be adequate if the displacement can be bidirectional so that scanning can also be bidirectional. The embodiments of FIGS. 6 and 7 illustrate means for providing bidirectional offsetting of a probe laser beam. The embodiment of FIG. 8 provides two axis displacement along a plane so that scanning in an arbitrary direction is possible. The embodiments described in FIGS. 6 through 8 are modifications of densitometer 10 shown in FIG. 1 with the incorporation of means for providing heating and probe beam displacement as mentioned previously. Various other of the described embodiments could also be modified to provide beam offsetting. Elements of the devices shown in FIGS. 6 through 8 which are identical to those shown in FIG. 1 are identified by like reference numbers.

FIG. 6 illustrates densitometer 140 which incorporates a tiltable glass plate 142 which is conventionally 0.25 to 0.5 inches thick and mounted to a device which allows the plate to be tilted so that refraction causes probe beam 27 to be offset in the plane defined by the beam and the scanned direction across gel slab 14. By adjusting the tilt angle of glass plate 142, the offset magnitude can be optimized for the selected scanning speed. The direction of the tilt can be reversed when the scan direction is reversed, thus providing the proper offset for bidirectional scanning. Adjustment over a range of one to five degrees would typically be required. Such angular adjustment can be made manually or by means of a electro-mechanical, piezoelectric or other electrically actuated device designated by reference number 144 in the drawing.

It will be found convenient to use glass plate 142 for densitometer 140 with parallel faces. In that case, the apparatus can be aligned with the faces of glass plate 142 perpendicular to the propagation direction of the probe beam which causes no offset. That orientation establishes a zero position for the system and allows coincident or other reproducible beam alignments. Further, if plate 142 has parallel faces, then equal tilt angles are used in both of the two scan directions, further simplifying operation.

A densitometer device in accordance with a sixth embodiment of this invention is shown in FIG. 7 and is generally designated by reference number 150. Apparatus 150 produces offsetting between the probe and heating beams 27 and 18, respectively, through the use of a weak cylinder lens 152 that is used as a variable refractor. It is necessary that the focal length of cylinder lens 152 be much greater than the focal length of any primary focusing lens in order to keep changes in the focal point of the probe beam 27 negligible. The ratio in focal length between the lenses should be at least 30 to 1. Thus, for a focusing lens with a focal length of thirty millimeters, cylindrical lens 52 having a focal length of 1,000 millimeters is adequate. Cylinder lens 152 is oriented with its longitudinal axis perpendicular to the scanning direction. If probe beam 27 intersects lens 152 at its center, no offset is produced. Translation of lens 152 by actuator 154, however, provides beam offset. Such translation can be made to occur in either direction, thus allowing bidirectional scanning.

A seventh embodiment of a densitometer in accordance with this invention is shown in FIG. 8 and is generally designated by reference number 160. This device is identical to those described with reference to FIGS. 6 and 7, except that offsetting of the probe and heating beams 27 and 18, respectively, is achieved using a weak biconvex or plano-convex lens 162. It is required that the lens 162 has a focal length which is long compared to the focal length of any primary focusing lens of the system, as explained with reference to FIG. 7. Operation of densitometer 160 is similar to that of densitometer 150 except that lens 62 is capable of generating offsets in any direction in the plane of gel sample 14. A zero offset condition is created when the probe beam 27 passes through the center of lens 162 and offset in the X direction is used to generate a beam offset in that direction and that offset can be reversed through reverse movement in the X direction. An offset in the Y direction can be achieved by displacing lens 162 in that direction. X-Y actuator 164 is used to property position lens 162.

While the above description constitutes the preferred embodiments of the present invention, it will be appreciated that the invention is susceptible to modification, variation and change without departing from the proper scope and fair meaning of the accompanying claims.

We claim:

1. A desitometer apparatus for evaluating electrophoresis gel samples for characterizing a presence of a dye within said sample comprising:
   means for emitting a heating beam for passing into said sample such that said dye absorbs energy from said heating beam, thereby locally heating said sample and generating a local index of refraction variation within said sample,
   means for emitting a probe beam for passing through said sample,
   translation means for causing said beams to sweep relative to said sample,
   beam aiming means for offsetting said probe beam with respect to said heating beam along the direction of translation of said beams with respect to said sample so that said probe beam passes through an area of said sample a predetermined period of time after said area is subjected to said heating beam, and
   detector means for evaluating the modification of said probe beam as said probe beam passes through said area, whereby said modification caused by said local index of refraction variations is related to the concentration of said dye within said sample.

2. A densitometer apparatus according to claim 1 wherein said heating beam is produced by a laser source.

3. A densitometer apparatus according to claim 1 wherein said probe beam is produced by a laser source.

4. A desitometer apparatus according to claim 1 wherein said detector means comprises an aperture and a photodetector whereby the modification of said probe beam as it passes through said sample is evaluated by illuminating said aperture and said photodetector such that the intensity measured by said photodetector is function of said modification.

5. A densitometer apparatus according to claim 1 wherein said heating beam emanates from a first laser source and said probe beam emanates from a second laser source, and further comprises means for orienting said heating beam and said probe beam in a parallel offset relationship as they pass through said sample, and
filter means for absorbing said heating beam after said beams pass through said sample such that only said probe beam is sensed by said detector means.

6. A densitometer apparatus according to claim 1 wherein said heating beam and said probe beam are derived from a single laser source and further comprising beam splitter means for providing a separated heating beam and probe beam.

7. A densitometer apparatus according to claim 1 wherein said heating beam and said probe beam are derived from a single laser source and further comprising means for separating the output from said laser by plane of polarization thereby providing said heating beam and said probe beam having orthogonally oriented axes of polarization.

8. A densitometer apparatus according to claim 7 further comprising filter means for absorbing light polarized in the direction of said heating beam.

9. A densitometer apparatus according to claim 1 further comprising chopper means for interrupting said heating beam and lock-in amplifier means for detecting the alternating component of the output from said detector means.

10. A densitometer apparatus according to claim 1 wherein said translation means comprises a translation stage for moving said sample relative to said beams.

11. A densitometer apparatus according to claim 1 wherein said beam aiming means comprises a glass plate positioned along said probe beam and tilted from a plane normal to said probe beam to cause said offsetting of said probe beam.

12. A densitometer apparatus according to claim 11 further comprising an actuator for varying the angle of tilt of said glass plate relative to said normal plane thereby varying the offset of said probe beam relative to said heating beam.

13. A densitometer apparatus according to claim 11 wherein said translation means provides bidirectional translation and further comprising an actuator for tilting said glass plate in opposite directions relative to said normal plane to enable bidirectional offsetting of said beam.

14. A densitometer apparatus according to claim 1 wherein said team aiming means comprises a cylinder lens positioned along said probe beam and displaceable to cause offsetting of said probe beam.

15. A densitometer apparatus according to claim 14 further comprising an actuator for adjusting the position of said cylinder lens thereby varying the offset of said probe beam relative to said beating beam.

16. A densitometer apparatus according to claim 14 wherein said translation means provides bidirectional translation and further comprising an actuator for adjusting the position of said cylinder lens to enable bidirectional offsetting of said beams.

17. A densitometer apparatus according to claim 1 wherein said beam aiming means comprises a lens conforming to surfaces of revolution generated about an axis and said axis being displaced from said probe beam to cause offsetting of said probe beam.

18. A densitometer apparatus according to claim 17 further comprising actuator means for enabling the position of said lens to be displaced relative to said axis along two orthogonal axes thereby displacing said probe beam along two orthogonal axes.

19. A densitometer apparatus according to claim 1 wherein said translation means causes said beams to sweep across said sample at a rate of 10–100 millimeters/seconds.

20. A densitometer apparatus according to claim 1 wherein the amount of said offset and the rate of translation of said beams relative to said sample are so related such that said predetermined period of time is 1–5 milliseconds.

* * * * *

UNITED STATES PATENT AND TRADEMARK OFFICE
CERTIFICATE OF CORRECTION

PATENT NO. : 4,938,593

DATED : July 3, 1990

INVENTOR(S) : Michael D. Morris; Konan Peck

It is certified that error appears in the above-identified patent and that said Letters Patent is hereby corrected as shown below:

On the front page, under heading "OTHER PUBLICATIONS", "Kohanzadek" should read --Kohanzadeh--.

On the front page, under heading "OTHER PUBLICATIONS", "Harris, Jr." should read --Harris, J.--.

On the front page, under heading "FILED", "August 10, 1988" should read --August 1, 1988--.

Column 1, line 65, "tedius" should read --tedious--.

Column 3, line 29, "team" should read --beam--.

Column 5, line 27, "lock-in" should read --Lock-in--.

Column 8, line 36, "property" should read --properly--.

Column 9, line 16, "comprises" should read --comprising--.

Column 10, line 15, "team" should read --beam--.

Column 10, line 21, "beating" should read --heating--.

Signed and Sealed this

Twelfth Day of November, 1991

*Attest:*

HARRY F. MANBECK, JR.

*Attesting Officer*   *Commissioner of Patents and Trademarks*